United States Patent
Mueglitz et al.

(10) Patent No.: US 11,621,886 B2
(45) Date of Patent: *Apr. 4, 2023

(54) METHOD FOR A WIRELESS DATA COMMUNICATION BETWEEN A SENSOR SYSTEM AND A RECEIVER, AND A SYSTEM FOR A WIRELESS DATA COMMUNICATION

(71) Applicant: Roche Diabetes Care, Inc., Indianapolis, IN (US)

(72) Inventors: Carsten Mueglitz, Schoenau (DE); Felix Bootz, Speyer (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/688,437

(22) Filed: Mar. 7, 2022

(65) Prior Publication Data

US 2022/0200853 A1 Jun. 23, 2022

Related U.S. Application Data

(63) Continuation of application No. 16/229,413, filed on Dec. 21, 2018, now Pat. No. 11,303,510, which is a
(Continued)

(30) Foreign Application Priority Data

Jun. 23, 2016 (EP) ..................... 16175960

(51) Int. Cl.
*H04L 41/0806* (2022.01)
*H04Q 9/00* (2006.01)
(Continued)

(52) U.S. Cl.
CPC ............ *H04L 41/0806* (2013.01); *A61B 5/00* (2013.01); *A61B 5/0002* (2013.01);
(Continued)

(58) Field of Classification Search
CPC .............. H04L 41/0806; H04W 76/16; H04W 52/0209; H04W 2209/883; H04W 84/18;
(Continued)

(56) References Cited

U.S. PATENT DOCUMENTS

| 8,622,903 B2 | 1/2014 | Jin et al. |
| 2004/0167587 A1 | 8/2004 | Thompson |

(Continued)

FOREIGN PATENT DOCUMENTS

| CN | 104885089 A | 9/2015 |
| EP | 2 011 283 B1 | 11/2009 |

(Continued)

OTHER PUBLICATIONS

International Search Report and Written Opinion of the International Searching Authority, PCT/EP2017/064959, dated Jul. 21, 2017, 10 pages.

*Primary Examiner* — An T Nguyen
(74) *Attorney, Agent, or Firm* — Bose McKinney & Evans LLP

(57) ABSTRACT

The disclosure relates to a method and a system for a wireless data communication between a sensor system and a receiver capable of receiving analyte values sensed by the sensor system in a continuous analyte monitoring. The method includes establishing an unconnected mode operation for the system. The receiver receives a first data package broadcasted by the sensor system that has first status data indicative of a device status and/or an analyte value status. The first status data is processed by a receiver controller. A connected mode operation is established for the system responsive to determining at least one of a critical device status and a critical analyte value status. The establishing includes establishing a communication channel between the sensor system and the receiver and receiving a second data
(Continued)

package transmitted by the sensor system in the receiver, the second data package comprising one or more analyte values.

12 Claims, 2 Drawing Sheets

Related U.S. Application Data continuation of application No. PCT/EP2017/064959, filed on Jun. 19, 2017.

(51) Int. Cl.
*A61B 5/145* (2006.01)
*A61B 5/00* (2006.01)
*G16H 20/60* (2018.01)
*G16H 40/63* (2018.01)
*G16H 20/17* (2018.01)
*H04W 76/15* (2018.01)
*H04W 52/02* (2009.01)
*H04W 84/18* (2009.01)

(52) U.S. Cl.
CPC ........ *A61B 5/0004* (2013.01); *A61B 5/14532* (2013.01); *A61B 5/14546* (2013.01); *G16H 20/17* (2018.01); *G16H 20/60* (2018.01); *G16H 40/63* (2018.01); *H04Q 9/00* (2013.01); *H04W 52/0209* (2013.01); *H04W 76/15* (2018.02); *A61B 2560/0209* (2013.01); *H04Q 2209/40* (2013.01); *H04Q 2209/82* (2013.01); *H04Q 2209/823* (2013.01); *H04Q 2209/883* (2013.01); *H04W 84/18* (2013.01)

(58) Field of Classification Search
CPC .............. A61B 5/0002; A61B 5/14532; A61B 560/0209; H04Q 9/00; H04Q 2209/40
See application file for complete search history.

(56) References Cited

U.S. PATENT DOCUMENTS

| | | |
|---|---|---|
| 2007/0100480 A1 | 5/2007 | Sinclair et al. |
| 2009/0118592 A1 | 5/2009 | Klitgaard |
| 2012/0071098 A1 | 3/2012 | Chebbo et al. |
| 2013/0027186 A1 | 1/2013 | Cinbis et al. |
| 2013/0076531 A1 | 3/2013 | San Vicente et al. |
| 2014/0184422 A1 | 7/2014 | Mensinger et al. |
| 2015/0123810 A1 | 5/2015 | Hernandez-Rosas et al. |
| 2015/0164391 A1 | 6/2015 | Hernandez-Rosas et al. |
| 2016/0081597 A1 | 3/2016 | Bhavaraju et al. |
| 2016/0183191 A1 | 6/2016 | Badam et al. |
| 2017/0172473 A1* | 6/2017 | Wedekind ............ A61B 5/0004 |
| 2017/0181628 A1* | 6/2017 | Burnette ................ A61B 5/746 |
| 2017/0281060 A1 | 10/2017 | Wedekind et al. |
| 2018/0027104 A1 | 1/2018 | Mandapaka et al. |
| 2019/0116088 A1 | 4/2019 | Mueglitz et al. |

FOREIGN PATENT DOCUMENTS

| | | |
|---|---|---|
| JP | 2012-519439 A | 8/2012 |
| WO | WO 2010/100013 A1 | 9/2010 |
| WO | WO 2014/158405 A2 | 10/2014 |
| WO | WO 2015/069797 A1 | 5/2015 |
| WO | WO 2015/094981 A1 | 6/2015 |

\* cited by examiner

METHOD FOR A WIRELESS DATA COMMUNICATION BETWEEN A SENSOR SYSTEM AND A RECEIVER, AND A SYSTEM FOR A WIRELESS DATA COMMUNICATION

RELATED APPLICATIONS

This application is a continuation of U.S. patent application Ser. No. 16/229,413, filed Dec. 21, 2018, which is a continuation of PCT/EP2017/064959, filed Jun. 19, 2017, which claims priority to EP 16 175 960.0, filed Jun. 23, 2016, all of which are hereby incorporated herein by reference in their entirety.

BACKGROUND

The present disclosure refers to a method for a wireless data communication between a sensor system and a receiver, a system for a wireless data communication, and a computer program product.

Glucose monitoring helps people with diabetes manage the disease and avoid its associated problems. A person can use the results of glucose monitoring to make decisions about food, physical activity, and medications. A common way to check glucose level is performing discontinuous monitoring. Such checking usually involves pricking a fingertip with an automatic lancing device to obtain a blood sample and then using a glucose meter to measure the blood sample's glucose level. Such monitoring may also be referred to as spot monitoring.

As an alternative or in addition, continuous glucose monitoring (CGM) may be applied. A system for CGM may use a body sensor inserted under the skin to check glucose levels. The sensor stays in place for several days to weeks or even longer and then must be replaced. A transmitter sends information about an analyte value or level indicative of the glucose level via wireless and/or wired data transmission from the sensor to a receiver such as monitor device.

WO 2015/094981 A1 discloses a method for prolonging life of a battery installed in an analyte sensor system. The method includes measuring a first analyte value at a first time and causing a transmission of the measured first analyte value along with a predicted second analyte value. Measure a second analyte value at a second time and determine whether a difference between the measured second analyte value and the predicted second analyte value is within a predefined range. Skip transmission of the measured second analyte value if the difference is within the predefined range.

U.S. Publication No. 2009/0118592 A1 discloses a medical system comprising a sensor unit and a receiving unit. The sensor unit is adapted to generate sensor data indicative of a time-dependent characteristic of a subject, and transmit data to a receiver at intervals determined by an analysis of time-dependent changes in the generated sensor data. The receiving unit is adapted to receive sensor data at a non-predetermined rate. It is proposed to skip the transmission of sensor data in case there is no or only a small change in an actual sensor data value. On the other hand, in case of rapid changes in sensor data values, sensor data may be transmitted at higher rate.

EP 2 011 283 B1 discloses a method for wireless transmission of data between components of a blood glucose system by initially setting the receiver activation frequency to a first frequency value upon switching from communication mode to power saving mode, and setting the receiver activation frequency to a second frequency value smaller than the first frequency value if no communication initiation data frame is received for a predetermined power saving timeout period.

U.S. Pat. No. 8,622,903 B2 discloses a monitoring system with a transmitter configured to transmit once every minute randomly in a window of time of plus or minus 5 seconds, i.e., in time hops. For conserving power the receiver does not listen for its associated transmitter during the entire 10 second receive window, but only at the predetermined time it knows the data package will be coming from the corresponding transmitter.

WO 2015/069797 A1 discloses a method for a wireless data communication between an analyte sensor system and a mobile device capable of wirelessly receiving analyte values from the analyte sensor system. The method comprises transmitting a first series of advertisement signals beginning at a first time; receiving a data connection request from a mobile device at a second time; establishing a data connection with the mobile device; transmitting a connection interval indicative of a difference between the second time and the first time to the mobile device; transmitting an analyte value; terminating the data connection with the mobile device; and causing a transceiver of the analyte sensor system to enter a sleep state. A first analyte value measured at a first time is transmitted with a predicted second analyte value, and it is determined whether a difference between the measured second analyte value and the predicted second analyte value is within a predefined range.

EP 2 973 082 A2 discloses a method for transmitting data between devices of an analyte monitoring system, the method comprises the steps: generating sensor data using a sensor electronics module electrically connected to a continuous analyte sensor; establishing a two-way communication channel between the sensor electronics module and the a display device and each of the sensor electronics module and display device transmitting at a first transmission power; and initiating a low power transmission mode responsive to sensing User input at User interface of the display device indicative of entering the mode, wherein the low power transmission mode comprises one or both of the sensor electronics module and the display device transmitting at a second transmission power that is lower than the first transmission power.

U.S. Publication No. 2015/0164391 A1 as cited in the extended European search report discloses an analyte sensor system configured to be worn by a user, comprising an analyte sensor, a transceiver configured to transmit and receive wireless signals, a battery, and a control module coupled to the transceiver and configured to determine that a remaining power level of the battery is below a predefined power level, and cause a change in one or more data transmission operations of the analyte sensor system.

SUMMARY

The present disclosure provides a method for a wireless data communication between a sensor system and a receiver, and a system for a wireless data communication for which the operation of collecting analyte data is improved. Specifically, energy or power consumption is reduced in the disclosed arrangement provided with the receiver and the sensor system.

According to an aspect of the present disclosure, a method for a wireless data communication between a sensor system and a receiver is provided. The receiver is capable of wirelessly receiving, from the sensor system, analyte values sensed by the sensor system in a continuous analyte monitoring. The method comprises establishing an unconnected mode operation for the sensor system and the receiver, and receiving, by the receiver, a first data package broadcasted by the sensor system. The first data package comprises first status data indicative of at least one of a device status and an analyte value status. The first status data are processed by a receiver controller. A connected mode operation is established for the sensor system and the receiver responsive to determining at least one of a critical device status and a critical analyte value status in the processing. The establishing is comprising establishing a communication channel between the sensor system and the receiver; and receiving, through the communication channel, a second data package transmitted by the sensor system to the receiver, the second data package comprising one or more analyte values.

According to another aspect, a system for wireless data communication, the system comprising a sensor system and a receiver is provided. The receiver is capable of wirelessly receiving, from the sensor system, analyte values sensed by the sensor system in a continuous analyte monitoring. The system is configured to establish an unconnected mode operation for the sensor system and the receiver; receive, by the receiver, a first data package broadcasted by the sensor system, the first data package comprising first status data indicative of at least one of a device status and an analyte value status; process the status data by a receiver controller; and establish a connected mode operation for the sensor system, and the receiver responsive to determining at least one of a critical device status and a critical analyte value status in the processing. The establishing is comprising establishing a communication channel between the sensor system, and the receiver; and receiving, through the communication channel, a second data package transmitted by the sensor system to the receiver, the second data package comprising one or more analyte values.

According to a further aspect, a computer program product is provided.

The connected mode may be established in response to user confirmation to be received in the receiver through a user input device. For example, in response to the determining of at least one of the critical device status and the critical analyte status a request for a user input may be outputted through a user interface of the receiver, e.g., a display which may be connected to the receiver controller. After receiving the user input provided in response to the user request output the connected mode operation is established. Thereby, user confirmation may be requested prior to establishing or re-establishing the communication channel provided in the connected mode.

Sending and/or receiving of the data packages may be handled by a transceiver in at least one of the receiver and the sensor system.

The receiver may be a mobile or portable receiver. The receiver may be provided in a mobile or portable device such as a handheld device, a laptop, a mobile phone, and a remote controller. The remote controller may be configured to control operation of a medical system such as a drug delivery medical system. As an alternative, the receiver may be provided in a none-mobile device such as a desktop computer.

The sensor which may also be referred to as analyte sensor or biosensor may be configured for monitoring an analyte in a bodily fluid. For example, a glucose value of a bodily fluid may be monitored. However, the technologies disclosed may be used with regard to other analytes as well.

The first data package may be free of any analyte value. In conclusion, in such alternative embodiment neither the status data nor the first data package as whole includes any actual analyte value.

In an embodiment, the broadcasting of data packages by the sensor may be distinguished from transmitting or sending data packages from the sensor system to the receiver through the communication channel. In the broadcasting the data packages may be sent out to any device located in an area covered by the sensor device and capable of receiving such data packages by wireless transmission. Differently, the data packages transmitted by the sensor system through the communication channel are directed to be received by the receiver to which the sensor system has been paired in a device pairing process before.

The data processing, by the receiver controller, aims at determining whether the status data are indicating at least one of a critical device status and a critical analyte status. With regard to the critical device status, a critical device status selected from the following group may be determined by the data processing: sensor session stopped; power supply (battery) low; sensor type incorrect for the sensor system; sensor malfunction; device alert; occurrence of device fault in the sensor system; and request for time synchronization between the sensor system and the receiver. As an alternative or in addition, the critical device status may indicate at least one of the following: sensor calibration not allowed; sensor calibration recommended; and sensor calibration required. The status data may be indicative of a sensor temperature being outside a sensor temperature range required for validly sensing analyte values.

With regard to the critical analyte value status, the status data may be indicative of an alert message. The alert message may be generated by the sensor controller in response to detecting at least one critical analyte value status from the following group: analyte value lower than a patient specific low analyte level; analyte value higher than a patient specific high analyte level; analyte value lower than a hypo level (hypoglycaemia); analyte value higher than a hyper level (hyperglycaemia); a rate of analyte value decrease is exceeding a limit; a rate of analyte value increase is exceeding a limit; analyte value lower than a sensitivity of the sensor system; and analyte value higher than a sensor limit.

The method may further comprise operating the receiver on a first power consumption level in the unconnected mode operation; and operating the receiver on a second power consumption level in the connected mode operation, the second power consumption level being higher than the first power consumption level. Operating the arrangement comprising the sensor system and the receiver on the different power consumption levels will save energy, thereby, extending the lifetime of the power supply such as a battery.

The method may further comprise establishing a sleeping mode operation for a functional unit of the receiver in the unconnected mode operation; and establishing an activated mode operation for the functional unit in the connected mode operation, wherein a power consumption level of the functional unit is higher in the activated mode operation compared to the sleeping mode operation.

The receiving of the first data package may comprise receiving, by the receiver, an unencrypted data package broadcasted by the sensor system, the unencrypted data package comprising the status data. The first data package as whole may be broadcasted and received without data encryption.

The method may further comprise establishing a secure communication channel between the sensor system, and the receiver, the secure communication channel being capable of communicating encrypted data packages; and receiving, through the secure communication channel, an encrypted data package included in the second data package, the encrypted data package comprising the one or more analyte values. The secure communication channel may be established or set-up in the device pairing process described in further detail below. The establishing or setting-up of the secure communication channel configured for secure and encrypted data transmission may comprise exchanging keys for secure data exchange (secure keys) between the two devices.

The establishing of the communication channel may comprise establishing a bidirectional communication channel between the sensor system and the receiver. The bidirectional communication channel will allow for sending and receiving data packages on both the receiver side and the sensor system side.

The method may further comprise maintaining the unconnected mode operation for the sensor system, and the receiver responsive to not determining both the critical device status and the critical analyte value status in the processing; and receiving a third data package broadcasted by the sensor system in the receiver, the third data package comprising further status data indicative of at least one of a present device status and a present analyte status. Neither the critical device status nor the critical analyte status is determined in the processing of the first status data. The receiver does not recognize need for establishing or re-establishing the communication channel between the sensor system and the receiver.

The method may further comprise providing device specific status data in the first data package; determining, by the receiver controller, whether the receiver controller is capable of processing the device specific status data; and processing the device specific status data by the receiver controller, if it is determined that the receiver controller is capable of processing the device specific status data, otherwise ignoring the device specific status data in the receiver. For example, a receiver from a device supplier may not be capable of correctly processing device specific data from a sensor system provided by a different device supplier because of a non-standard data exchange protocol. Still, in response to the ignoring the status data the connected mode of operation may be established. Thereby, the transmission of the one or more analyte value to the receiver may be performed without having determined at least one of a critical device status and a critical analyte value status. It shall avoid a critical situation just because of failing to process the status data in the receiver. A higher level of safety may be reached. Loss of critical status data can be avoided.

The status data may be provided by a status flag or a status data field. In such embodiment or in other embodiments the status data may comprise one or more codes, e.g., alphanumeric codes, to which is assigned at least one of the critical analyte value status and the critical device status. In the receiver assignment between the one or more codes and the critical status is provided which allows the receiver controller to determine the critical status from processing the status data comprising the one or more codes. Such code may be provided in the status flag or the status data field. In response to determining the status flag or the status data field in the receiver, a user warning may be output by the receiver, the user warning may comprise output of at least one of video data and sound data.

The establishing of the connected mode operation may further comprise performing a device pairing process for the sensor system, and the receiver responsive to determining at least one of the critical device status and the critical analyte value status in the processing. The device pairing process may comprise establishing a secure and encrypted connection for data transmission between the receiver and the sensor system. The establishing or setting-up of the connection (communication channel) configured for secure and encrypted data transmission may comprise exchanging keys for secure data exchange (secure keys) between the two devices.

After the initial device pairing has been completed, reconnection may be done without repeating device pairing or key exchange. Reconnecting comprises establishing the communication channel between the sensor system and the receiver again after the connection was interrupted or stopped, for example, during the time period between successive events of data transmission defined by time intervals. Following, after the re-establishing of the connection between the devices analyte values detected by the sensor may be received in the receiver. In an embodiment, control signals may be transmitted from the receiver to the sensor system, the control signals defining a time delay between the end of the device connection process which is establishing the communication channel and the starting point of transmitting the one or more analyte values to the receiver. As an alternative, the time period can be determined in relation to the point in time at which a former transmission of one or more analyte values was started.

The method may further comprise receiving, by the receiver, a fourth data package broadcasted by the sensor system, the fourth data package comprising second status data indicative of at least one of the device status and the analyte value status; processing the second status data by the receiver controller; and re-establishing the connected mode operation for the sensor system and the receiver responsive to determining at least one of the critical device status and the critical analyte value status in the processing, the re-establishing comprising re-establishing the communication channel between the sensor system and the receiver; and receiving, through the communication channel, a fifth data package transmitted by the sensor system in the receiver, the fifth data package comprising one or more further analyte values. Once the device pairing has been performed for the sensor system and the receiver, the communication channel may be re-established without pairing the devices again.

With regard to a glucose measurement or monitoring, a glucose level or value may be determined by analyzing a blood sample via, e.g., spot monitoring, and, as an alternative or in addition, by continuous glucose monitoring (CGM) via a fully or partially implanted sensor. In general, in the context of CGM an analyte value or level indicative of a glucose value or level in the blood may be determined. The analyte value may be measured in an interstitial fluid. The measurement may be performed subcutaneously or in vivo. CGM may be implemented as a nearly real-time or quasi-continuous monitoring procedure frequently or automatically providing/updating analyte values without user interaction. In an alternative embodiment, analyte may be measured with a biosensor in a contact lens through the eye fluid or with a biosensor on the skin via transdermal measurement in sudor.

The alternative embodiments described above may apply to the system for a wireless data communication or transmission mutatis mutandis.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following description. Rather, the embodiments are chosen and described so that others skilled in the art may appreciate and understand the principles and practices of this disclosure.

Figure 1:
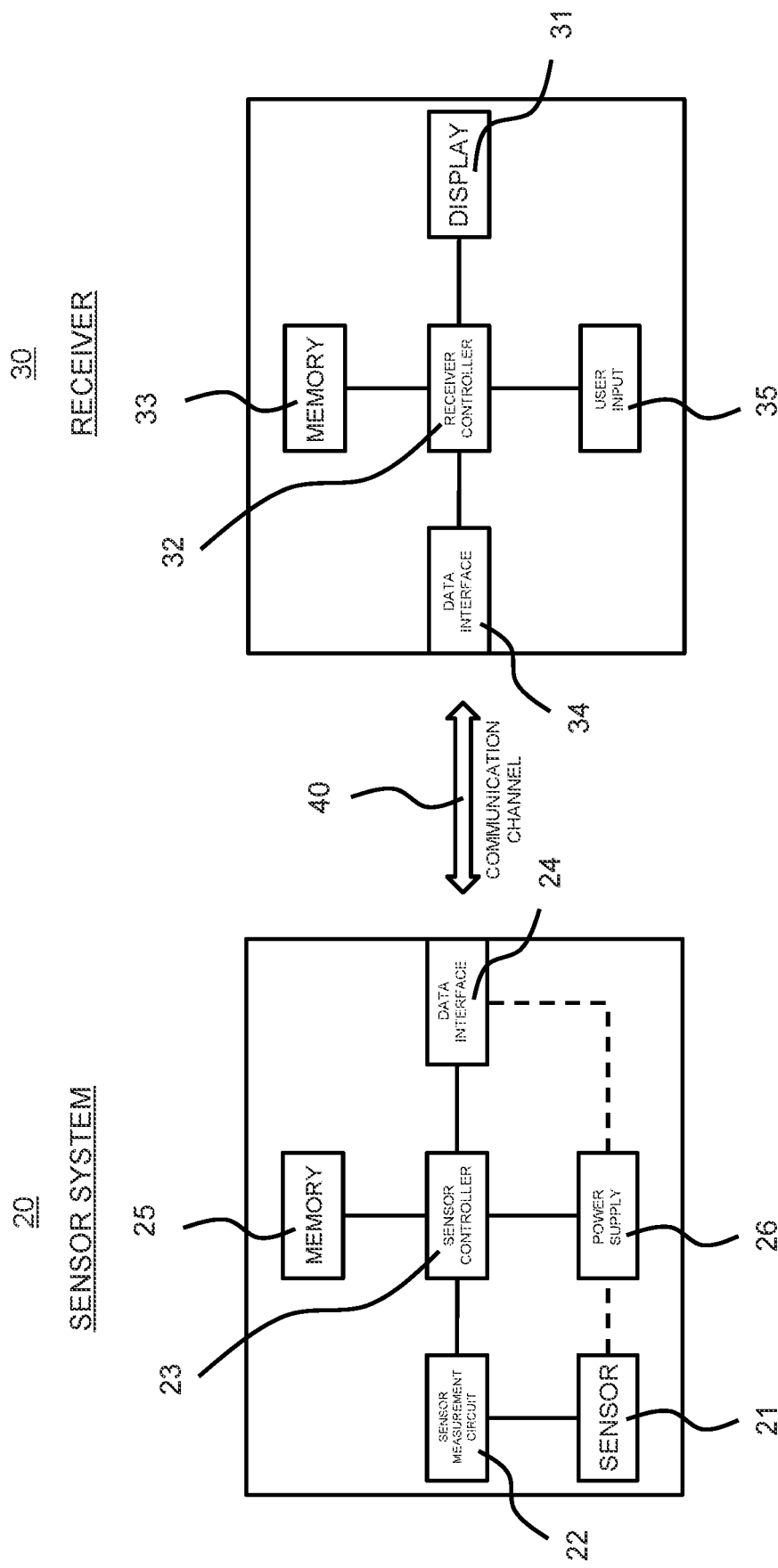
FIG. 1 is a schematic representation of elements of a continuous analyte monitoring system comprising a sensor system and a receiver.

FIG. 1 shows schematic representation illustrating elements of embodiments of a continuous analyte monitoring system 10 comprising a sensor system 20 and a receiver 30.

The analyte sensor system 20 may include a sensor 21 which may be provided as analyte sensor or biosensor. The sensor 21 is capable of sensing analyte values for an analyte in a fluid such as a bodily fluid. The sensor 21 is coupled to a sensor measurement circuit 22 providing for, e.g., processing and managing sensor data. The sensor measurement circuit 22 may be coupled to a sensor controller 23 comprising one or more processors. In some embodiments, the sensor controller 23 may perform part or all of the functions of the sensor measurement circuit 22 for obtaining and processing sensor measurement values (analyte values) from the sensor 21.

The sensor controller 23 is further coupled to a data interface 24 for sending sensor data. The data interface 24 may be provided with a transceiver configured to send and receive data through a communication channel 40. The data interface 24 which may be capable of receiving requests and commands from an external device, such as the receiver 30, which, for example, is used to receive data packages from the sensor system 20 through wireless data transmission.

According to the exemplary embodiment, the sensor system 20 further includes a memory 25 for storing data, e.g., sensor data indicative of the analyte values. The memory 25 may also be used for storing an operating system for a custom application designed for wireless data communication between the sensor system 20 and the receiver 30. The memory 25 may be a single memory device or multiple memory devices and may be a volatile or non-volatile memory for storing data and/or instructions for software programs and applications. The instructions may be executed by the processor(s) of the sensor controller 23 to control and manage the data interface 24.

Components of the sensor system 20 may require replacement periodically. For example, as shown in FIG. 1, the sensor 21 may be provided in the sensor system 20 that includes the sensor measurement circuit 22, the sensor controller 23, the data interface 24, the memory 25, e.g., a transceiver, and a power supply 26 such as a battery. The sensor 21 may be an implantable sensor.

The sensor 21 may require periodic replacement, e.g., every 7 to 30 days. The sensor measurement circuit 22 may be configured to be powered and active for much longer than the sensor 21, e.g., for three, six months or more, until the battery needs replacement. Replacing these components may be difficult and require the assistance of trained personnel. Reducing the need to replace such components, particularly the battery, significantly improves the convenience of the sensor system 20 to the user.

Still referring to FIG. 1, the receiver 30 may include a display 31 for outputting video information to a user. The display 31 is coupled to a receiver controller 32 providing for, e.g., processing and managing data. The receiver controller 32 may comprise one or more processors. Further, the receiver 30 may be provided with a memory 33 coupled to the receiver controller 32. The receiver controller 32 is further coupled to a data interface 34 for receiving data packages from the sensor system 20 through the communication channel 40. The data interface 34 may be capable of receiving requests and commands from an external device, and of sensing data through wireless data transmission, for example, to the sensor device 20.

According to the embodiment in FIG. 1, the receiver 30 has a user input device 35 connected to the receiver controller 32. User input may be received through the user input device 35.

The receiver 30 may be provided in a mobile or portable device such as smartphone, mobile phone, laptop computer, hand-held computing device or personal digital assistant.

In some embodiments, a sensor session may correspond to the life of the sensor 21, e.g., in the range of 7 to 30 days. When the sensor system 20 is used for the first time or re-activated once a battery has been replaced in some cases, a sensor session may be established. There may be a process for initially establishing communication between the receiver 30 and the sensor system 20 when it is first used or re-activated (e.g., the battery is replaced). Such initial process may comprise a device pairing process.

In case of a first or initial device connecting and prior to actually receiving one or more analyte values in the receiver 30, a so-called device pairing process is provided between the receiver 30 and the sensor system 20. In general, the device pairing process is the initial process for establishing the connection for data transmission between the receiver 30 and the sensor system 20. By the pairing process a unidirectional or bidirectional data transmission line or connection is established between the devices. In response to finalizing the device pairing which is known as such, e.g., with regard to pairing Bluetooth devices, through the communication channel 40, the one or more analyte values may be transmitted immediately or in a timely delayed fashion from the sensor system 20 to the receiver 30.

Prior to the device pairing process, the sensor system 20 may by continuously broadcasting a signal "ready for pairing." Such signal indicates that the sensor system 20 may be paired with some other device for transmitting data. In response to detecting the signal "ready for pairing," the receiver 30 may start the pairing process for establishing the connection for data transmission between the receiver 30 and the sensor system 20.

Once the receiver 30 and the sensor system 20 have established communication, specifically by establishing the communication channel 40, the receiver 30 and the sensor system 20 may periodically or non-periodically be in communication over the life of several sensors until, for example, the battery needs to be replaced. Each time the sensor 21 is replaced, a new sensor session may be established. The new sensor session may be initiated through a process completed using the receiver 30 and the process may be triggered by notifications of a new sensor via the communication between the sensor system 20 and the receiver system 30 that may be persistent across sensor sessions.

After completion of the pairing process, the communication channel may be interrupted, e.g., because of missing need for data transmission between the sensor system 20 and the receiver 30. For re-establishing the communication channel 40 there may be no need for device pairing again. Rather, the communication channel 40 may be established between the sensor system 20 and the receiver 30 without repeating device pairing. Once the communication channel is interrupted the sensor system may continuously broadcast a signal "ready for connecting/establishing the communication channel." Such signal indicates that the sensor system 20 may be connected to the receiver 30 for transmitting data again. In response to detecting the signal which may be broadcasted as an unencrypted signal, the receiver 30 may start the connecting process, thereby re-establishing the communication channel 40.

Wireless communication protocols may be used to transmit and receive data between the sensor system 20 and the receiver 30. The wireless protocol used may be designed for use in a wireless sensor network that is optimized for periodic or aperiodic and small data transmissions to and from multiple devices in a close range, e.g., a personal area network (PAN). For example, the protocol may be optimized for periodic or aperiodic data transfers where transceiver units may be configured to transmit data for short intervals and then enter low power modes for long intervals.

The wireless communication protocol may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support short-distance and/or low-power wireless communication such as peer-to-peer, start, tree, or mesh network topologies such as WiFi, Bluetooth and Bluetooth Low Energy (BLE). The wireless protocol may operate in various frequency bands such as an open ISM band such as 2.4 GHz.

In some embodiments, when a standardized communication protocol is used, commercially available transceiver circuits or units may be utilized that incorporate processing circuitry to handle low level data communication functions such as the management of data encoding, transmission frequencies, handshake protocols, and the like. In these embodiments, the receiver controller 32/the sensor controller 23 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver circuit.

The sensor system 20 gathers analyte values detected by from the sensor 21 that it may send to the receiver 30 in a periodical or aperiodic fashion. Data points are gathered and transmitted over the life of the sensor 21, e.g., in the range of 1 to 30 days or more. New measurements may need to be transmitted often enough to adequately monitor glucose levels in a bodily fluid. Rather than having the transmission and receiving elements of both the sensor system 20 and the receiver 30 continuously communicating, the sensor system 20 and the receiver 30 may establish the communication channel 40 between them based on periodic or sporadic need requirements.

Referring still to FIG. 1, the exemplary system or arrangement depicted includes the sensor system 20 communicatively coupled to the receiver 30 through the data interfaces 24, 34 which, e.g., may be implemented with a transceiver unit. The coupling is provided for transmitting biological or analyte data indicative of properties of an analyte such as glucose from the sensor system 20 to the receiver 30. In case of using transceivers, the data interface 25 provides for a sensor-side transceiver. The sensor system 20 is provided with a sensor-side transceiver configured for transmitting and receiving electronic data.

The biological or analyte data received in the receiver 30 at least in part may be stored in the memory 33. The sensor 21 may be provided as body sensor at least in part implantable into a human body.

In one embodiment, the sensor 21 is a glucose sensor configured to detect or sense a glucose level (e.g., glucose concentration) when placed just under the skin of a patient. Specifically, a subcutaneously placed sensor may be provided. For example, the sensor 21 can be a disposable glucose sensor that is worn under the skin for a few days until replacement is needed. As is noted above, the sensor system 20 is communicatively coupled with the receiver 30. Accordingly, in the case of a glucose sensor, the sensor system 20 can be communicatively coupled with, for example, a hand held device such as a smart phone or a remote controlling device, or a smart glucose meter and can provide ambulatory CGM data, i.e., glucose data that is sampled continuously throughout the lifetime of the sensor 21. The receiver 30 provided in such hand held device may control the data transmission from the sensor system 20 to the handheld by initiating transmission of analyte values.

Figure 2:
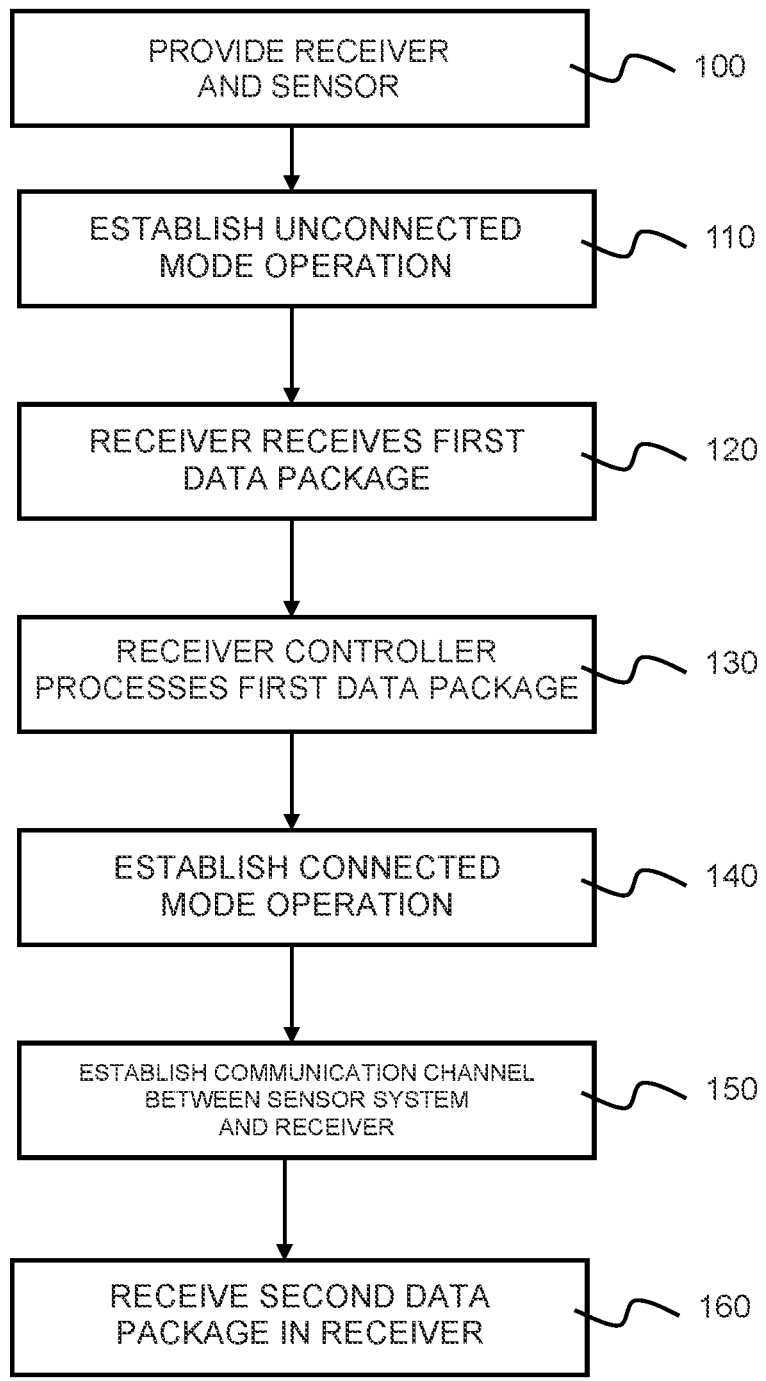
FIG. 2 is a schematic representation with regard to a method for wireless data communication between the sensor system and the receiver capable of wirelessly receiving, from the sensor system, analyte values sensed by the sensor system in a continuous analyte monitoring.

Referring to the schematic representation in FIG. 2, an embodiment of a method for wireless data communication between the sensor system 20 and the receiver 30 capable of wirelessly receiving, from the sensor system 20, analyte values sensed by the sensor 21 in a continuous analyte monitoring is described. The continuous analyte monitoring, for example, can be a continuous glucose monitoring.

In step 100 the receiver 30 and the sensor system 20 are provided.

In step 110 an unconnected mode operation is established for the sensor system 20 and the receiver 30. In the unconnected mode operation the communication channel 40 is interrupted. Rather, the receiver 30 is listening to signals or data packages broadcasted by the sensor system 20. Such mode of operation may be referred to as listen mode operation. For example, the sensor system 20 may broadcast a so-called advertisement signal which indicates that the sensor system 20 is ready for setting-up a connection for data transmission. Such process may comprise a device pairing process which may in turn comprises establishing the communication channel 40.

In the unconnected mode operation the receiver 30 may receive signals and/or data packages broadcasted by the sensor system 20 via the data interface 34. In step 120 the receiver 30 is receiving a first data package comprising status data from the sensor system 20. The status data are indicative of at least one of a device status and an analyte status. The device status provides information about the status of the sensor system 20 and/or the status of a component of the sensor system 20 such as the sensor 21. The analyte status may refer to specific information about the analyte values sensed by the sensor 21. For example, in case of glucose level monitoring, a critical analyte value status may indicate a hypo level (hypoglycaemia) or a hyper level (hyperglycaemia). The analyte status may be free of any information about an actual analyte value such as a glucose level value. The status data may be provided by a status flag or a data field within the first data package received in the receiver 30.

The first data package received in the receiver 30 is processed by the receiver controller 32 in step 130. For example, the data processing aims at determining whether the status data are indicating at least one of a critical device status and a critical analyte status. With regard to the critical device status, a critical device status selected from the following group may be determined by the data processing: sensor session stopped; power supply (battery) low; sensor type incorrect for the sensor system; sensor mail function; device alert; occurrence of device fault in the sensor system; and request for time synchronization between the sensor system and the receiver. As an alternative or in addition, the critical device status may indicate one of the following: sensor calibration not allowed; sensor calibration recommended; and/or sensor calibration required. The status data may be indicative of a sensor temperature being outside a sensor temperature range required for validly sensing analyte values.

With regard to the critical analyte value status, the status data may be indicative of an alert message. The alert message may be generated by the sensor controller 23 in response to detecting at least one critical analyte value status from the following group: analyte value lower than a patient specific low analyte level; analyte value higher than a patient specific high analyte level; analyte value lower than a hypo level (hypoglycaemia); analyte value higher than a hyper level (hyperglycaemia); a rate of analyte value decrease is exceeding a limit; a rate of analyte value increase is exceeding a limit; analyte value lower than a sensitivity of the sensor system; and analyte value higher than a sensor limit.

In step 140, in response to determining at least one of the critical device status and the critical analyte value status a connected mode operation is established for the sensor system 20 and the receiver 30. The establishing of the connected mode operation comprises establishing the communication channel 40 between the sensor system 20 and the receiver 30 in step 150.

Further, in step 160 a second data package from the sensor system 20 is received in the receiver 30. The second data package comprises one or more analyte values sensed by the sensor 21 in the continuous analyte monitoring measurement. The second data package may be received as an encrypted data package in the receiver 30. Contrary, the first data package may be transmitted without encryption from the sensor system 20 to the receiver 30.

The unconnected mode operation and the connected operation, respectively, require a different power consumption level in the receiver 30 and/or the sensor system 20. For example, in the unconnected mode operation at least one component of the receiver 30 such as the input device 35 and/or the display 31 may be in a sleeping mode, thereby, having a reduced power or energy consumption. There may be even no power consumption in the sleeping mode operation. In response to establishing the connected mode operation, one or more functional components of the receiver 30 and/or the sensor system 20 may be switched to a functional or activated mode operation from the sleeping mode operation, thereby, increasing the level of power consumption for such functional component(s) in the receiver 30 and/or the sensor system 20, respectively, as whole.

Maintaining the system for wireless data transmission comprising the sensor system 20 and the receiver 30 in the unconnected mode operation will save energy or power compared to the connected mode operation. Only if the status data indicate need for device connection (connected mode operation) the unconnected mode operation is left for switching to the connected mode operation.

The application of the unconnected and the connected mode operation as outlined above may be applied to different use scenarios of the system comprising the sensor system 20 and the receiver 30. For example, the unconnected mode operation may be maintained overnight, the nighttime being a daytime for which the user may be not interested in receiving analyte values from the sensor system 20. Still, the status data received in the receiver 30 will ensure that device connection, i.e., establishing or re-establishing the communication channel 40, is automatically initiated in case at least one of the critical device status and the critical analyte value status is detected. In such case, a warning message may be outputted to the user, e.g., through the display 31.

Another embodiment may refer to a time period in which the user may be not disturbed by receiving analyte values in the receiver 30, for example, while visiting a theatre or a cinema. Again, the status data received in the receiver 30 will ensure that analyte values are transmitted from the sensor system 20 to the receiver 30 if the critical device status and/or the critical analyte value status are detected.

In the different embodiments described above, the unconnected mode operation may be established in response to a user input. As an option, the user may define a predefined time period for the establishing of the unconnected mode operation, e.g., several hours. Only in case the critical device status and/or the critical analyte value status is determined in the receiver 30 after receiving the first data package comprising the status data, the unconnected mode operation may be stopped for switching to the connected mode operation.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A receiver, comprising:
a processor;
a memory; and
a data interface;
wherein the receiver is configured to:
  wirelessly receive analyte values from a continuous analyte monitoring sensor;
  receive a first data package broadcasted by the continuous analyte monitoring sensor, the first data package having analyte value status data;

process the analyte value status data;
determine from the processed analyte value status data a critical analyte value status;
establish a connected mode operation for the receiver and the continuous analyte monitoring sensor; and
receive a second data package transmitted by the continuous analyte monitoring sensor, the second data package comprising one or more analyte values.

2. The receiver of claim 1, wherein the receiver is a drug delivery system controller.

3. The receiver of claim 1, wherein the receiver is configured to run in a first power consumption mode while running in an unconnected mode.

4. The receiver of claim 3, wherein the receiver is configured to run in a second power consumption mode while running in the connected mode.

5. The receiver of claim 4, wherein the first power consumption mode is lower than the second power consumption mode.

6. The receiver of claim 1, wherein the receiver is a smart phone.

7. The receiver of claim 1, wherein a secure communication channel configured to communicate encrypted data packages between the continuous analyte monitoring sensor and the receiver is established for the connected mode operation.

8. The receiver of claim 7, wherein the second data package is an encrypted data package.

9. A drug delivery system, comprising:
a pump; and
a receiver, comprising:
a processor;
a memory; and
a data interface;
wherein the receiver is configured to:
wirelessly receive analyte values sensed by a continuous analyte monitoring sensor;
receive a first data package broadcasted by the continuous analyte monitoring sensor, the first data package having analyte value status data;
process the analyte value status data;
determine from the processed analyte value status data a critical analyte value status;
establish a connected mode operation for the receiver and the continuous analyte monitoring sensor; and
receive a second data package transmitted by the continuous analyte monitoring sensor, the second data package comprising one or more analyte values.

10. The drug delivery system of claim 9, wherein the receiver is configured to run in a first power consumption mode while running in an unconnected mode.

11. The drug delivery system of claim 10, wherein the receiver is configured to run in a second power consumption mode while running in the connected mode.

12. The drug delivery system of claim 11, wherein the first power consumption mode is lower than the second power consumption mode.

* * * * *